United States Patent
Lehmann et al.

(10) Patent No.: US 8,303,587 B2
(45) Date of Patent: Nov. 6, 2012

(54) EXTERNAL FIXATOR ELEMENT

(75) Inventors: Philippe Lehmann, Lamboing (CH); Roland Thomke, Bellach (CH)

(73) Assignee: Stryker Truama S.A. (CH)

( * ) Notice: Subject to any disclaimer, the term of this patent is extended or adjusted under 35 U.S.C. 154(b) by 931 days.

(21) Appl. No.: 11/702,935

(22) Filed: Feb. 6, 2007

(65) Prior Publication Data
US 2007/0233061 A1 Oct. 4, 2007

(30) Foreign Application Priority Data

Mar. 31, 2006 (EP) ..................................... 06112136

(51) Int. Cl.
*A61F 5/04* (2006.01)
(52) U.S. Cl. ............................................ 606/59; 606/54
(58) Field of Classification Search .............. 606/53–60; 600/184–242
See application file for complete search history.

(56) References Cited

U.S. PATENT DOCUMENTS

| | | | | |
|---|---|---|---|---|
| 4,612,921 A | * | 9/1986 | Lazo de Zbikowski | 606/57 |
| 4,620,533 A | * | 11/1986 | Mears | 606/54 |
| 4,745,913 A | * | 5/1988 | Castaman et al. | 606/59 |
| 5,042,462 A | | 8/1991 | Bremer | |
| 5,098,432 A | * | 3/1992 | Wagenknecht | 606/54 |
| 5,571,103 A | * | 11/1996 | Bailey | 606/62 |
| 5,891,144 A | | 4/1999 | Mata et al. | |
| 5,969,747 A | * | 10/1999 | Egan | 347/256 |
| 6,299,930 B1 | * | 10/2001 | Marotta et al. | 427/2.28 |
| 7,074,294 B2 | * | 7/2006 | Dubrow | 156/276 |
| 2003/0149436 A1 | * | 8/2003 | McDowell et al. | 606/73 |
| 2004/0005473 A1 | * | 1/2004 | Matteucci et al. | 428/515 |
| 2004/0020286 A1 | * | 2/2004 | Blakley et al. | 73/204.26 |
| 2004/0133199 A1 | * | 7/2004 | Coati et al. | 606/54 |
| 2004/0250950 A1 | * | 12/2004 | Dubrow | 156/276 |
| 2005/0038425 A1 | * | 2/2005 | Werding et al. | 606/54 |
| 2005/0038498 A1 | * | 2/2005 | Dubrow et al. | 623/1.15 |
| 2005/0119656 A1 | * | 6/2005 | Ferrante et al. | 606/59 |
| 2006/0122596 A1 | * | 6/2006 | Dubrow | 606/60 |
| 2006/0204738 A1 | * | 9/2006 | Dubrow et al. | 428/292.1 |
| 2006/0267397 A1 | * | 11/2006 | Possarnig et al. | 301/95.102 |

FOREIGN PATENT DOCUMENTS

| | | |
|---|---|---|
| ES | 2246744 A1 * | 2/2006 |
| JP | 2000-505331 A | 5/2000 |
| JP | 2004-275762 A | 10/2004 |
| WO | WO-86/07568 | 12/1986 |
| WO | 97/30651 A2 | 8/1997 |

OTHER PUBLICATIONS

Office Action from Japanese Application No. 2007-078309 dated Jan. 17, 2012.

* cited by examiner

*Primary Examiner* — Alvin Stewart
*Assistant Examiner* — Lynnsy Schneider
(74) *Attorney, Agent, or Firm* — Lerner, David, Littenberg, Krumholz & Mentlik, LLP

(57) ABSTRACT

A polymeric external fixator element, such as a rod or a pin or a clamp, has at least one contacting surface. At least one of the contacting surfaces of the element responsible to establish connection between the element and a different external fixator element is provided with a rough ablated structure. The clamping can be improved if one of the polymeric elements comprise fibers having fiber parts protruding above the surface.

17 Claims, 5 Drawing Sheets

EXTERNAL FIXATOR ELEMENT

CROSS-REFERENCE TO RELATED APPLICATION

The present application claims priority from European Patent Application No. 06112136.4 filed on Mar. 31, 2006, the disclosure of which is incorporated herein by reference.

BACKGROUND OF THE INVENTION

The invention relates to mechanical elements that are used by external fixators and methods to manufacture such mechanical elements.

External fixators are well known by prior art, for example from U.S. Pat. No. 5,891,144, the disclosure of which is incorporated herein by reference. Such external fixators are used for stabilizing two parts of a fractured bone and holding the parts of the bone in the correct position during the healing process. Typically external fixators comprise several pins for bony attachment, rods or bars for holding the position of the pins and clamping means for connecting the pins with the rods. These external fixator elements are usually made of stainless steel, titanium or aluminum.

U.S. Publication No. 2006/0039750, the disclosure of which is incorporated herein by reference, shows a polymeric clamp.

Weight considerations, especially for long term patients wearing an external fixator for extended periods of time, request a further change of material towards plastic or polymeric based materials, as well as the request to have X-ray transparency of the device. However, it is a drawback of external fixator elements of such prior art, especially when rods are made of such light weight materials, that rods may change the position relative to the clamp and therefore to other rods and pins over time due to frictional problems.

SUMMARY OF THE INVENTION

An aspect of the present invention is to provide an element, a method and an external fixator system, contributing to the enhancement of the connection between clamps and rods and pins of an external fixator.

According to an embodiment of the invention there is provided an external fixator element, e.g., for example, a rod, a pin or a clamping device which comprises at least one contacting surface. At least one of the contacting surfaces of the element responsible for establishing a connection between said element and a different external fixator element is provided with a rough ablated structure.

The term ablated surface comprises opening the surface to a gas stream having abrasive elements such as sand-blasting, brushing or similar procedures which erode the surface and especially etching.

The invention is based on the insight that a bearing having a plastic material on plastic material combination has a low friction coefficient, wherein it is possible, according to the invention, to change the low friction coefficient of plastic material when fibers parts are protruding over the surface of the plastic material. Therefore, a plastic element according to a preferred embodiment comprises fibers having parts protruding over the surface, thus enhancing the roughness of the surface and improving the grip of a jaw of a clamp onto a rod.

These and other aspects of the invention are provided for by an external fixator which may include a rod, a pin and a clamping element having a pair of jaws which can grip the rod or pin. At least one of the clamp or the rod or the pin is made of a polymeric material having fibers embedded or formed therein. The polymeric/fiber clamp, rod or pin has a surface in which ends of the fibers are exposed. The surface may be produced by a blade of techniques such as sand blasting or etching. The matrix or carrier material containing the fibers may be a polyamide, polypropylene, PEEK, polyacetal and polyesterepoxide. The fibers embedded may be glass fibers, carbon fibers or halymid fibers. Preferably free ends of the fibers protrude from the contacting surface of the clamp, rod or pin. One of the external fixation elements such as the rod, pin or clamp may be made of metal such as stainless steel, aluminum or titanium.

The surface roughness may also be made by brushing the polymeric contact surface with a wire brush, etching with nitric or sulfuric acid or using abrasive elements in a gas stream such elements as a glass beads, metal pellets, dry ice, powdered abrasives, powdered slag or sand. In general, one of the elements will be made of metal and the other being made of the polymer having the exposed fiber ends.

BRIEF DESCRIPTION OF THE DRAWINGS

The drawings will be explained in greater detail by means of a description of an exemplary embodiment, with reference to the following figures.

DETAILED DESCRIPTION

Figure 1:
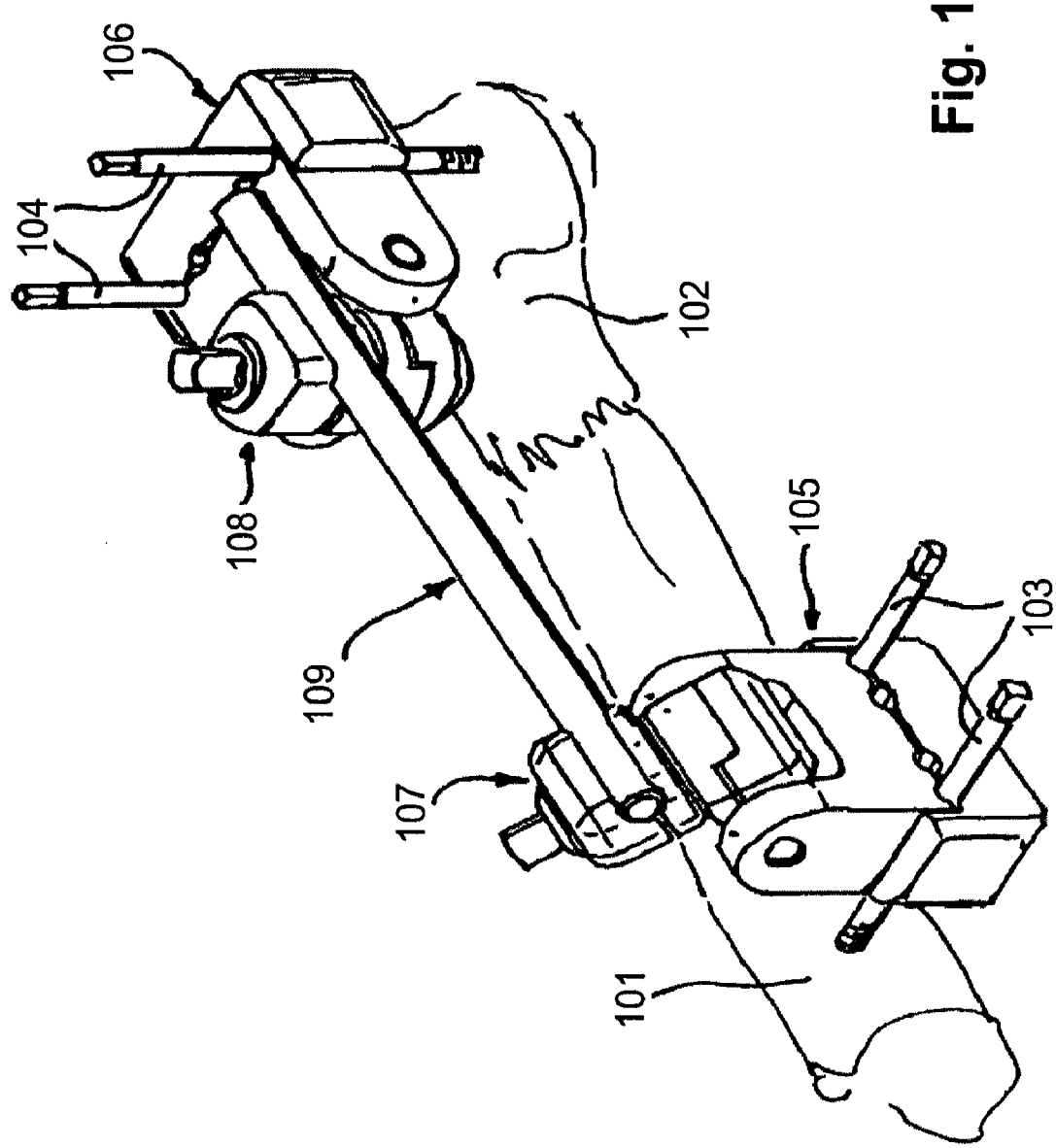
FIG. 1 shows an example of an external fixator with different external fixator elements.

FIG. 1 shows an example of an external fixator as an example. Such an external fixator typically comprises several pins 103, 104, a rod 109 and clamping means 105, 106, 107, 108, these elements designated as external fixator elements. An external fixator is used to stabilize and to correct the direction of a fractured bone during the healing process. Typically, several pins 103, here two, are introduced into the first part of the bone 101 and several pins 104, here two, are introduced into the second part of the bone 102. Clamping means 105, 106, 107, 108 are used to establish a mechanical connection between the pins 103, 104 and the rod 109. With the aid of the rod 109 and the clamping means 105, 106, 107, 108, the direction of the first part of the bone 101 relative to the second part of the bone 102 is adjusted.

Surfaces of the pins 103, 104 of rod 109 and of the clamping means 105, 106, 107, 108, which face each other upon installation of the external fixators, are designated as contacting surfaces. As an example, rod 109 is introduced in an opening of the clamping means 107. Thereby, the surface that is covered on the rod 109 by the clamping means 107 is designated as contacting surface. But also the surface that is covered by the rod 109 on the clamping means 107, in this case the surface of the opening, is also designated as contacting surface. In the external fixator as shown in FIG. 1, such contacting surfaces of rods have typically a cylindrical shape. Clamps may have a complementary cylindrical shape or, in a cross-section view, creating a hollow triangle, providing longitudinal lines of contact between the clamp jaw and the rod or pin.

For the sake of simplicity pins 103, 104, rod 109 and clamping means 106, 107, 108, 109 are designated as mechanical elements further on. However, it is understood to a person skilled in the art that the term mechanical element is not limited to the ones just named.

Figure 2:
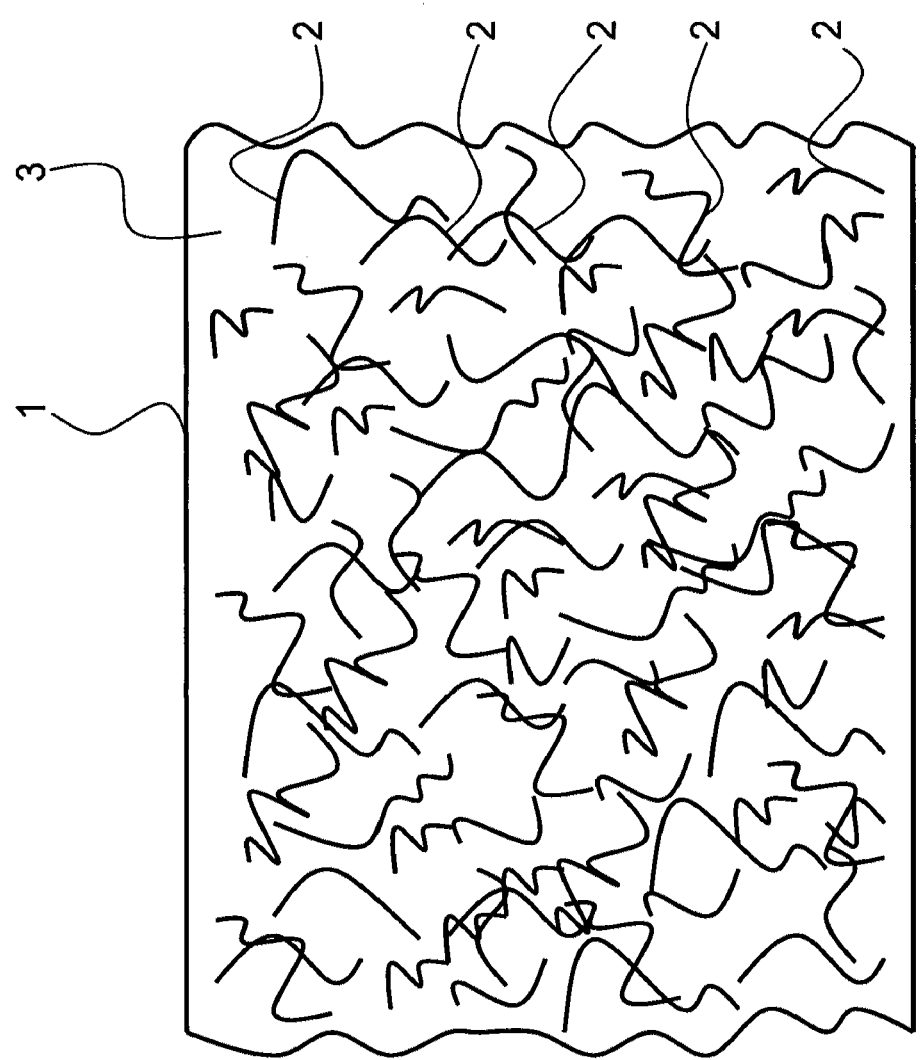
FIG. 2 shows schematically a cross section through an external fixator element like a rod.

FIG. 2 shows schematically a part of a cross section of a mechanical element. Reference numeral 1 designates a line being part of an untreated contacting surface of the mechanical element.

In this embodiment the mechanical element shown is made out of fiber-reinforced plastic. Fibers 2 are surrounded by a carrier material or plastic 3.

Such a mechanical element can be manufactured by a plurality of different molding techniques e.g. and including, for example, thermoplastic and thermoset injection molding, blow molding, rotational molding, thermoforming, structural foam molding, compression molding, resin transfer molding (RTM) and others.

Such a mechanical element can be manufactured by a die-casting method. The fibers 2 are arranged randomly. It may be seen that the fibers 2 do not extend over the surface 1. This is due to the manufacturing process of such a fiber-reinforced plastic. The fibers 2 placed in the mold before casting tend to stay in a distance from the surface 1, i.e., no free fiber ends are touching or are directly aligned within the uppermost surface layer.

Figure 4:
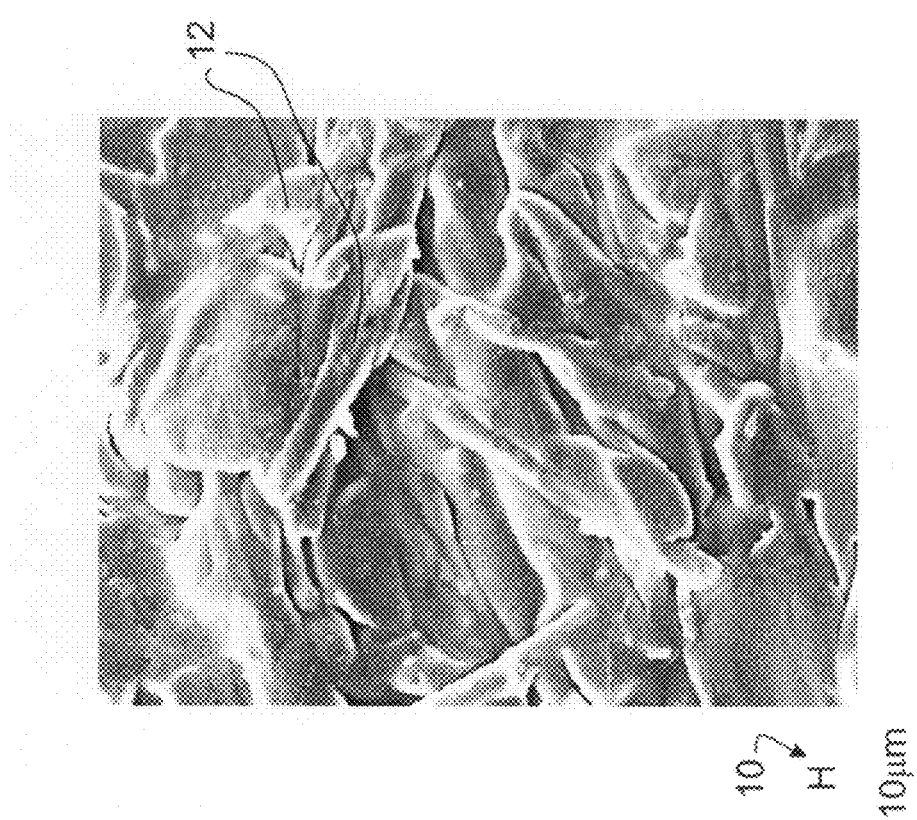
FIG. 4 shows a microscopic image of a surface of an element like and according to FIG. 2.

The tested embodiments shown in FIG. 4 were produced with thermoplastic molding, wherein the fibers were already mixed with the plastic material and brought together in the form. The portion of fibers as part of the mixture can be chosen between 20 and 70 percent by volume, preferably between 30 and 60 percent by volume, or between 40 to 50 percent by volume.

Figure 3:
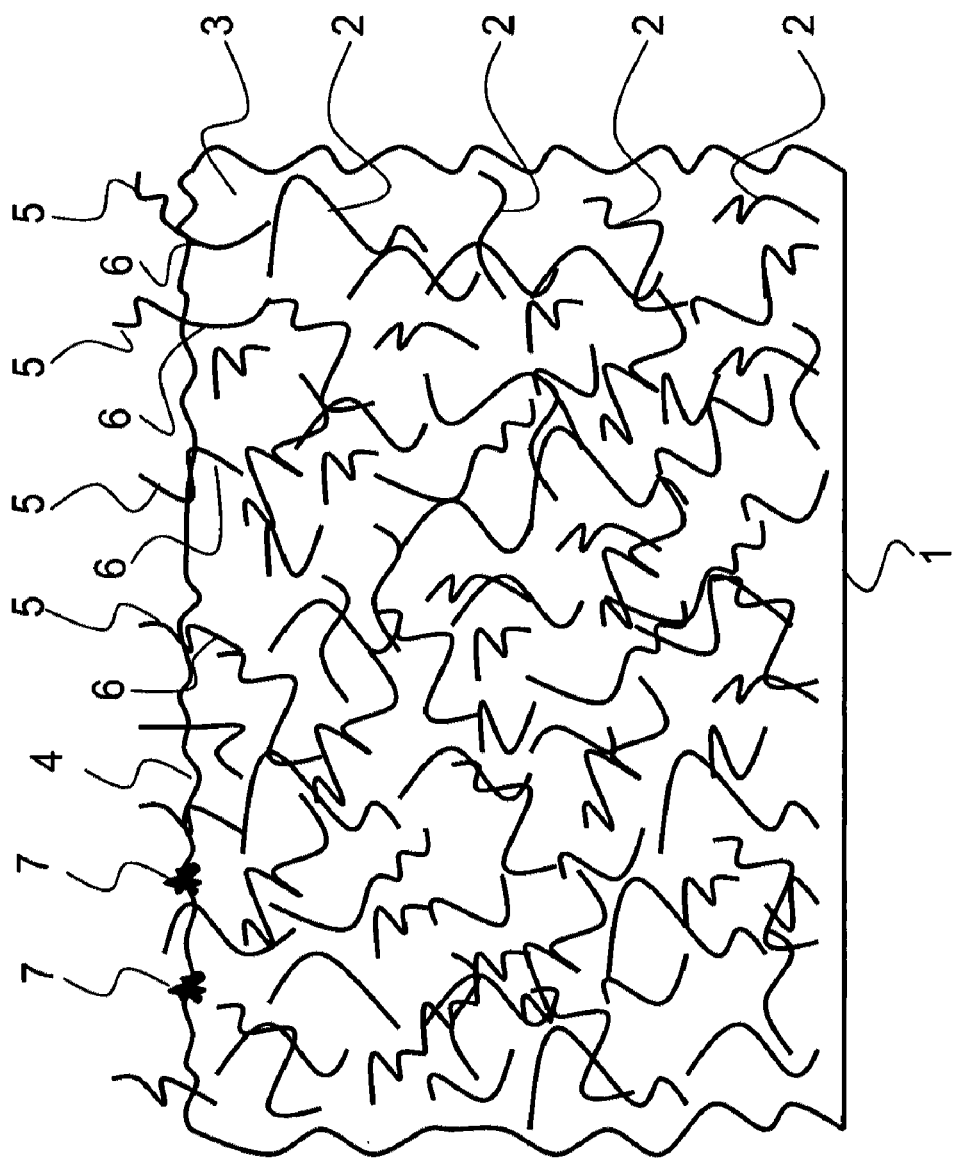
FIG. 3 shows schematically a cross section through an external fixator element according to the present invention.

FIG. 3 shows schematically a part of a cross section of a mechanical element according to an embodiment of the invention. Reference numeral 4 designates a roughened or treated contacting surface according to a method of the present invention of the mechanical elements, for example, of the rod 109.

In this first embodiment, the material of the mechanical element is preferably fiber-reinforced plastic. Thereby, the plastic is reinforced by glassfibers, carbonfibers, or aramid-fibers or other suitable fibers. It is even possible that cotton-fibers may be used for this purpose. Preferably, the fibers have a length between 0.1 millimeter and 2 millimeter. Even more preferably, the fibers have a length between 0.25 millimeter and 1 millimeter. Preferably the fibers have a diameter between 25 micrometer and 1500 micrometer. Even more preferably, the fibers have a diameter between 50 micrometer and 200 micrometer. The plastic is preferably a plastic chosen from the group of (in the case of injection molding) polyamide, polypropylene, PEEK, polyacetal and (in the case of RTM, lamination or pultrusion, carbon epoxy pultrusion) polyester epoxide.

In this first embodiment, a treated surface 4 is the result of a method according to the present invention. According to this method, the untreated surface 1 will be exposed to a gas stream comprising abrasive elements. This is also designated as sandblasting. The abrasive elements allow a steady abrasion or removal of the surface 1, meaning that parts of the surface 1 will be removed and the treated surface 4 results. Pressurized air may be used as a gas stream. The abrasive elements are preferably chosen from the group of sand, glass beads, metal pellets, dry ice, powdered slag or powdered abrasives. However other abrasive elements that are known by the person skilled in the art may also be used. The size of the abrasive element may vary since they influence the degree of abrasion of the surface of the mechanical element. Possible sizes of abrasive elements comprise 200 micrometer to 1000 micrometer.

The degree of abrasion of the surface 1 depends on the distance between the surface 1 and the fibers 2. Thus, the degree of abrasion of the first surface is reached, when some of the fibers 2 protrude from the treated surface 4. Thereby, a fixed part 6 of the fiber 2 is still firmly connected to the plastic; a protruding part 5 of the fiber 2 protrudes from the surface 4.

Due to the sandblasting process, the roughness of the treated surface 4 is much higher than the roughness of the untreated surface 1, thus resulting in an enhanced friction between the contacting surfaces of the mechanical elements. Due to the protrusion of the fibers 2, the friction between the contacting surfaces of the mechanical elements is increased furthermore. Measurements have shown that friction increased over 50% if the surface 4 is rough and the fibers protrude from the surface 4 accordingly in comparison to untreated surfaces. In case the protruding parts 5 of the fibers 2 fray, the friction is enhanced additionally.

If the degree of abrasion is higher than necessary, it is possible that some fibers will become detached from the plastic 3. Such fibers will be removed by the pressurized gas stream of the sandblasting process. Therefore, contamination due to loose fibers is not an issue.

Depending on the material of the plastic part, it is also possible that some of the abrasive elements remain as a (e.g., sand) corn 7 in the treated surface 4 with the result that the friction between the contacting surface is enhanced even more. The dimension of such embedded corns 7 depends on the abrasive materials used and can be between 250 micrometer and 500 micrometer.

FIG. 4 shows the surface 1 of a mechanical element manufactured, as explained in connection with FIG. 2, in a microscopic zoomed view. The fiber content of the specimen is rather high. The dimension of the photograph can be seen from the bar 11 showing a length of 10 micrometer. It is clearly visible that the surface is not planar, but it shows a myriad of elevations. However, the height of such elevations is rather small. The height is typically in the range of several ten micrometer or can even be lower than one micrometer. There can be seen covered fibers 12. These fibers 12 are covered with a layer of the plastic material of the mixture. This layer of plastic material together with a corresponding plastic surface of a clamp shows said low friction coefficient.

Figure 5:
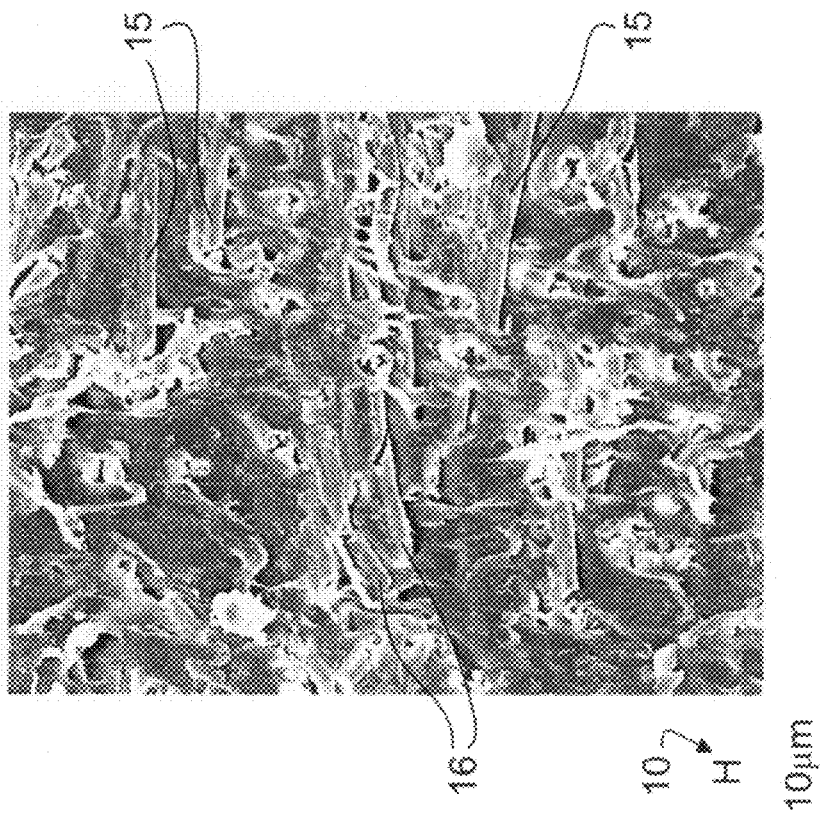
FIG. 5 shows a microscopic image of a surface of an element like and according to FIG. 4.

FIG. 5 shows a surface of the specimen FIG. 4 in a microscopic enlarged view after sand-blasting treatment. Of course, the photograph does not represent the identical part of the specimen but a portion which is perhaps a millimeter apart. In comparison to FIG. 4, it may be seen that the surface has changed dramatically. The protruding parts 5 of the fibers 6 from the schematical representations are now visible as uncovered fibers 15. There are at least two differences. Parts of fibers oriented in the direction or plane of the surface are no longer covered by plastic material. Therefore, this portion of the fiber surface having a different friction behavior than the plastic material together with a corresponding plastic surface of a clamp, shows a far higher friction coefficient. Secondly, the elevations are more pronounced. Additionally, there are sharp fiber ends 16 protruding out of the plane of the surface of the element.

Figure 6:
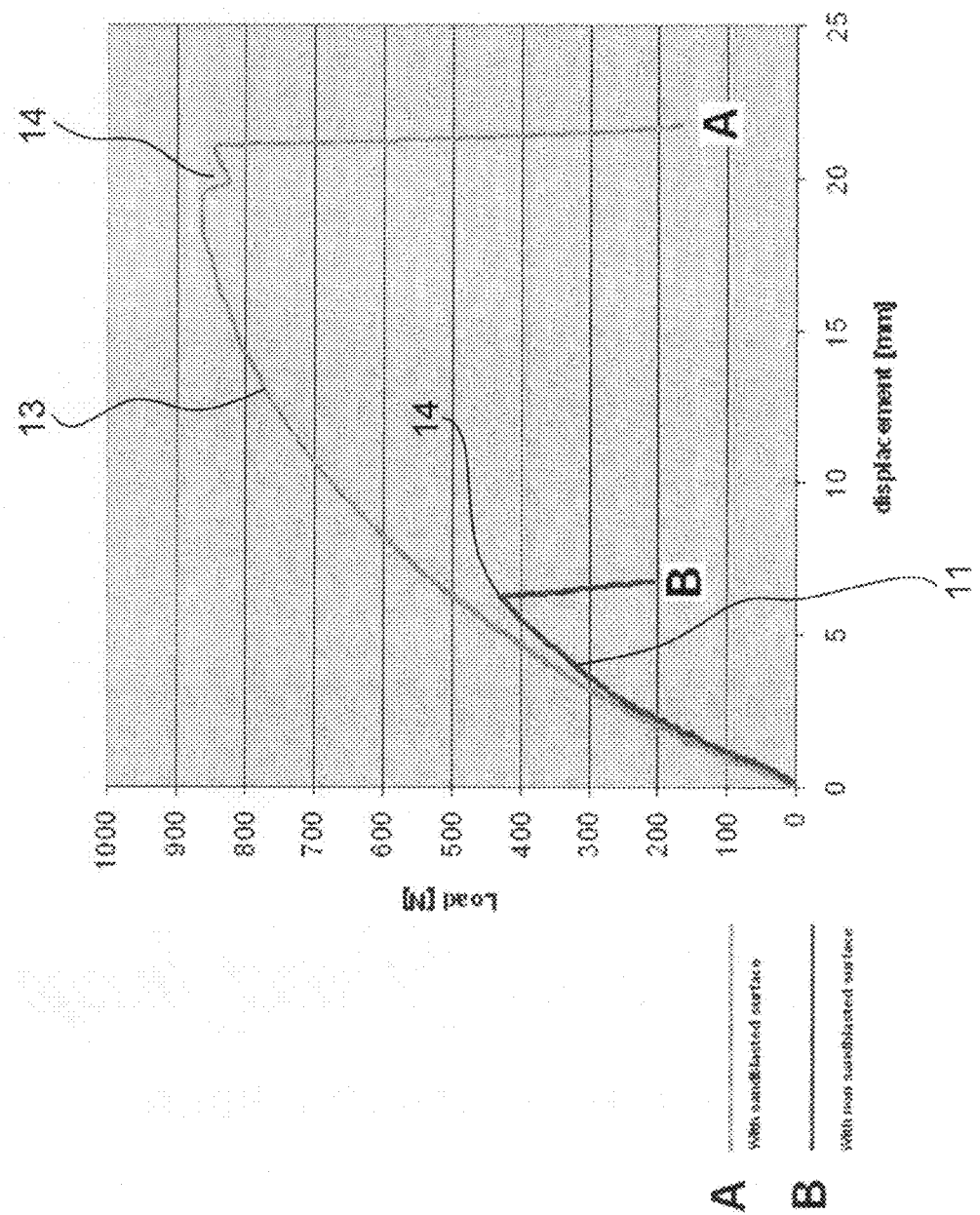
FIG. 6 shows diagrammatically the measured difference between a device according to prior art and a device according to the present invention.

FIG. 6 shows a graph of a test with a rod that has a surface of non-treated plastic and with a rod that has a treated surface according to present invention. The figure shows the behavior, if a force is applied to the connected parts, e.g., the rod is clamped using a clamp having an untreated plastic material surface. The failure 14 occurs when connected parts start to slide. With a sandblasted surface, the sliding occurs, if at all, much later with higher forces than without sandblasting. The diagrams show the displacement of the rod against the applied force to clamp the rod. The untreated rod shows a slightly faster sliding 11 until approximately 400 Newton, when the failure 14 takes place. The treated rod can withstand a load 13 of over 800 N until the failure happens.

Reference is now made to FIG. 1. It may be seen that the position of the contacting surfaces on the rod 109 depend on the distance between the pins 103, 104. Here it is possible to designate the whole surface of the rod 109 as contacting surface. Therefore, it is advantageous that whole surface of the rod 109 will be roughened, i.e., treated as described above. However, it may also be possible that only parts of the surface of the rod 109 are treated. If that is the case, the parts are preferably arranged in the end parts of the rod 109.

The contacting surfaces of the clamping elements 107, 108 are also treated with a method as described above. Thereby, the clamping means 107, 108 comprises typically two contacting surfaces. A first contacting surface is in contact with the rod 109 and a second contacting surface is in contact with the pins 103, 104. Here the same applies as it does for the rod 109. Thereby, it is possible that the whole contact surface or just parts of it will be treated with a method according to the present invention. It is also possible to treat both surfaces or just the first contacting surface or just the second contacting surface.

The sandblast method as described above may also be applied to the pins 103, 104. But due to the fact that the one end of pins is introduced into the human body, the method is preferably to be applied to the other free end of the pins 103, 104 in order to prevent possible infections, and pins are often made of stainless steel.

It is particularly advantageous when all the contacting surfaces of all mechanical elements will be treated by the method according to the present invention. This takes the best advantage of the method.

But it is also possible that only certain surfaces will be treated. As an example, it is possible that only the surface of the rod 109 will be treated, but not the contacting surface of the clamping elements 107, 108. The friction here will be lowered.

In a further embodiment it is also possible that the surface 1 will be brushed, e.g. this may be done by using a fast rotating steel wire brush, engaging the surface of a slowly rotating rod. Such a brush can also be introduced into the cavity of a clamp, brushing one or both inner clamp surfaces as it would be in the place of a rod. However, it is also possible to use non-rotating brushes with longitudinal movements.

In a further embodiment, it is also possible that the surface 1 will be etched away by means of an acid such as nitric or sulphuric acid. The acid is applied to the surface 1 of a fiber-reinforced plastic element until the degree of removal of the surface reaches the desired state. A treated surface 4 results. This is the case when the fibers protrude from the surface as described above. The etching can also be conducted using a strong oxidizing solution as hydrogen peroxide.

Other methods can be performed to achieve the rough ablated structure, enabling an improved grip of the external fixator element, especially when used in a set, comprising one or more clamps having treated ablated jaw clamping surfaces of rods or pins having a similar treated ablated surface.

In further embodiment not shown, it is also possible that mechanical elements are made without any fibers. Here the surface that is rougher as before will be responsible for the enhanced friction. In a preferred embodiment, such mechanical elements are made out of plastics or stainless steel or titanium. It has to be seen that the main advantage of the invention can be realized when the low friction coefficient plastic-plastic material is to be enhanced. When there are no fibers in both clamping and clamped parts, then the plastic material will deform and loose the roughness over a time of some days or weeks. Therefore a non-exposed fiber clamp-and-rod combination can only be used over a limited time frame.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An external fixator element comprising a rod, a bone pin, and a clamp, the bone pin having a surface contacting the clamp, the rod having an end contacting the clamp, at least part of a contacting surface between the rod, the pin surface, and the clamp, which surface is responsible for an interconnection therebetween, being provided with a rough ablated polymeric structure,
    wherein the external fixator element contacting surface is made out of a fiber-reinforced polymer that comprises a carrier material and partially embedded fibers,
    wherein the partially embedded fibers have a length between 0.1 millimeter and 2 millimeter,
    wherein exposed free ends of said fibers protrude from the contacting surface wherein corns are embedded in the contacting surface, the corns having a diameter between 250 and 500 micrometer.

2. The external fixator element according to claim 1, wherein the fibers are selected from a group consisting of glassfibers, carbonfibers and aramidfibers.

3. The external fixator element according to claim 1, wherein at least one of the rod, pin or clamp has a body made out of a metal, selected from the group consisting of stainless steel, aluminum and titanium.

4. The external fixator element according to claim 1, wherein the polymer material is selected from a group consisting of polyamide, polypropylene, PEEK, polyacetal and polyester epoxide.

5. The external fixator element according to claim 4, wherein the fibers are selected from a group consisting of glassfibers, carbonfibers and aramidfibers.

6. The external fixator element according to claim 1, wherein the fibers have a length between 0.25 millimeter and 1 millimeter.

7. An external fixator element comprising a rod and a metal pin having first and second ends and a clamp, the rod and the pin first end have a contacting surface for contacting a contacting surface of the clamp, the pin second end capable of insertion into tissue, at least one of the contacting surfaces between the rod and the clamp and the pin first end and the clamp, which surface is responsible for an interconnection therebetween, being provided with a rough ablated polymeric structure, the polymeric structure having reinforcing fibers embedded therein extending outwardly from the contacting surface in a direction or plane of the surface, the reinforcing fibers having a length greater than 0.1 millimeter and less than 2 millimeters, wherein corns are embedded in the contacting surface, the corns having a diameter between 250 and 500 micrometer.

8. The external fixator element according to claim 7, wherein the fibers are selected from a group consisting of glassfibers, carbonfibers and aramidfibers.

9. The external fixator element according to claim 7, wherein at least one of the rod, pin or clamp has a body made out of a metal, selected from the group consisting of stainless steel, aluminum and titanium.

10. The external fixator element according to claim 7, wherein free ends of the fibers protrude from the contacting surface.

11. The external fixator element according to claim 7, wherein the polymer material is selected from a group consisting of polyamide, polypropylene, PEEK, polyacetal and polyester epoxide.

12. The external fixator element according to claim 11, wherein the fibers are selected from a group consisting of glassfibers, carbonfibers and aramidfibers.

13. An external fixator element comprising a rod, a bone pin, and a clamp, the bone pin having an surface for engaging bone and an external surface contacting the clamp, the rod having an end contacting the clamp, at least part of a contacting surface between the rod, the external pin surface, and the clamp, which surface is responsible for an interconnection therebetween, being provided with a rough ablated polymeric structure, wherein the external fixator element contacting surface is made out of a fiber-reinforced plastic that comprises a carrier material and fibers, wherein the fibers have a length between 0.1 millimeter and 2 millimeter, wherein free ends of said fibers protrude from the contacting surface, wherein corns are embedded in the contacting surface, the corns having a diameter between 250 and 500 micrometer.

14. The external fixator element according to claim 13, wherein the fibers are selected from a group consisting of glassfibers, carbonfibers and aramidfibers.

15. The external fixator element according to claim 13, wherein at least one of the rod, pin or clamp has a body made out of a metal, selected from the group consisting of stainless steel, aluminum and titanium.

16. The external fixator element according to claim 13, wherein the polymer material is selected from a group consisting of polyamide, polypropylene, PEEK, polyacetal and polyester epoxide.

17. The external fixator element according to claim 16, wherein the fibers are selected from a group consisting of glassfibers, carbonfibers and aramidfibers.

* * * * *